United States Patent

Yoda et al.

[11] Patent Number: 5,234,403
[45] Date of Patent: Aug. 10, 1993

[54] BLOOD COLLECTING APPARATUS

[75] Inventors: Takumi Yoda, Takatsuki; Takeshi Fuji, Nishinomiya; Soichi Tanaka, Nara; Mamoru Nishijima, Machida; Yasunobu Izumi; Mitsuhiro Ida, both of Yokohama, all of Japan

[73] Assignees: Sumitomo Bakelite Co., Ltd., Tokyo; Kurray Co., Ltd., Okayama, both of Japan

[21] Appl. No.: 705,211

[22] Filed: May 24, 1991

[30] Foreign Application Priority Data

May 25, 1990 [JP] Japan .................................. 2-134076
Jul. 26, 1990 [JP] Japan ............................. 2-080094[U]

[51] Int. Cl.$^5$ ............................................ A61M 37/00
[52] U.S. Cl. ................................. 604/4; 604/6; 604/317; 210/650
[58] Field of Search ................ 417/274; 604/4–6, 604/317–319, 321, 403, 405, 406; 210/650

[56] References Cited

U.S. PATENT DOCUMENTS

| | | | |
|---|---|---|---|
| 3,965,896 | 6/1976 | Swank | 604/4 |
| 3,993,560 | 11/1976 | Halpern | 604/4 |
| 4,047,526 | 9/1977 | Reynolds et al. | 604/4 |
| 4,266,545 | 5/1981 | Moss | 417/274 |
| 4,976,707 | 12/1990 | Bodicky et al. | 604/4 |
| 5,055,198 | 10/1991 | Shettigar | 604/319 |

Primary Examiner—Randall L. Green
Assistant Examiner—R. Clarke
Attorney, Agent, or Firm—Browdy and Neimark

[57] ABSTRACT

A blood collecting apparatus for collecting and reserving blood lost from the patient during or after operation, wherein thrombus contained in the collected blood is removed, and it is possible to prevent the new generation of the thrombus. The apparatus may readily be used safely. The apparatus includes a blood collecting container, a suction pipe having a branched pipe provided with a sterilizing filter, a collecting pipe provided with a port for supplying a blood anti-coagulant and a blood filter, and a discharge pipe having a blood filter. These pipes are connected to an upper part of the container. A suction unit is connected to an end portion of the suction pipe. A catheter or the like is connected to the end of the collecting pipe. The suction unit is operated to suck and collect the blood from the incision during or after the operation.

10 Claims, 4 Drawing Sheets

BLOOD COLLECTING APPARATUS

The present invention relates to an apparatus for collecting and reserving blood lost from a patient during or after the operation, and retransfusing the blood to the patient himself or herself.

In view of a fear of infection of AIDS and hepatitis, a problem of immune reaction against external proteins, or saving of reserved blood per se, recently, a self-transfusion has been frequently used for sucking and collecting blood, overflowing during the surgical operation, of the patient himself or herself from the incised or operated part and returning the blood back to the patient through washing and filtration.

For instance, in the case of the incision operation of heart or the like while connecting an artificial lung to the human body, the blood flowing out of the incision of the operated part (which blood is usually mixed with and diluted by water solution with broken ice for cooling the heart muscles) is collected into a reservoir, and moisture contained the blood collected in the reservoir is removed by a centrifugal separator or an ultra filtration membrane. Thereafter, the condensed blood is returned back to the human body (see Artificial Organs, 15(2), 1039 to 1042 (1986), for example).

On the other hand, however, in the plastic surgical operation or the like, the blood flowing from the incision after the operation is different from the blood flowing from the incision of the heart or the like in that a large amount thrombus is contained in the blood. Thus, the blood is to be disposed without any collection.

The self-blood collection and transfusion systems are generally divided into two types, i.e., a non-washing type and a washing type as follows: The non-washing type is such a system that the collected blood is simply returned back through the blood filter or the like. The application of this type is limited to the operation for a chest trouble, in view of the safety aspect. In contrast, the washing type system is composed of a blood introduction part, a reservoir for reserving the blood, a pump for sucking the blood, a means, such as a centrifugal separator or the like (generally used), for condensing the blood, and a blood return bag. These components are connected to each other. It has been however desired to provide the system whose suction mechanism may be individually managed or controlled for safe and simple blood collection and transfusion.

Thus, there has not yet been provided a simple blood collection and retransfusion apparatus with a suction device, suitable for a satisfactory system that is capable of collecting and filtrating the blood from the incision particularly after the operation and of returning the blood back through washing.

In many cases in an artificial groin joint replacement operation or an artificial knee joint replacement operation, the amount of the blood after the operation is 400 to 1,000 ml. For this reason, in many cases, the transfusion would be necessary. It is therefore expected to reduce the necessary amount of the transfusion by collecting the blood, after the operation, which has been conventionally disposed, and returning it back to the patient for the self-transfusion.

SUMMARY OF THE INVENTION

In view of the foregoing status of the self-blood collection and transfusion, an object of the invention is to provide a blood collecting and retransfusion apparatus for collecting blood from the patient himself or herself, used in combination with a washing and condensing apparatus, which collecting apparatus reserves the blood from the patient by sucking and collecting the blood at a suitable pressure, in which it is possible to supply a blood anti-coagulant in an effective manner, to remove generated thrombus and to feed the blood to the washing and condensing apparatus in a safety manner without contamination by the atmosphere.

The present inventors have studied and developed the apparatus which can collect the blood in a closed system without mixture of thrombus or the like in the discharged blood during or after the operation, thereby making the present invention.

According to the present invention, there is provided a blood collecting apparatus comprising: a blood collecting container for collecting blood discharged from an incised or operated part; a suction pipe adapted to be connected to a suction means; a collecting pipe for introducing the discharged blood to the blood collecting container; and a discharge pipe for discharging the discharged blood collected in the blood collecting container; each of the suction pipe, the collecting pipe and the discharge pipe having one end connected to an upper part of the blood collecting container; the suction pipe having a branched pipe provided at its atmospheric port with a sterilizing filter and with a valve means; a valve means being provided between the branched pipe and an end of the suction pipe; the collecting pipe having a branched pipe provided with a port for supplying a blood anticoagulant; a blood filter being interposed between the last-mentioned branched pipe and the blood collecting pipe; a valve means being provided between the blood filter and the blood collecting container; one end portion, connected to the upper portion of the blood collecting container, of the discharge pipe extending to be opened to a bottom of the container, the other end portion thereof being provided with a blood filter; and a valve means being provided between the blood collecting container and the last-mentioned blood filter.

DESCRIPTION OF THE PREFERRED EMBODIMENTS

A blood collecting apparatus according to the invention will now be described with reference to the accompanying drawings.

Figure 1:
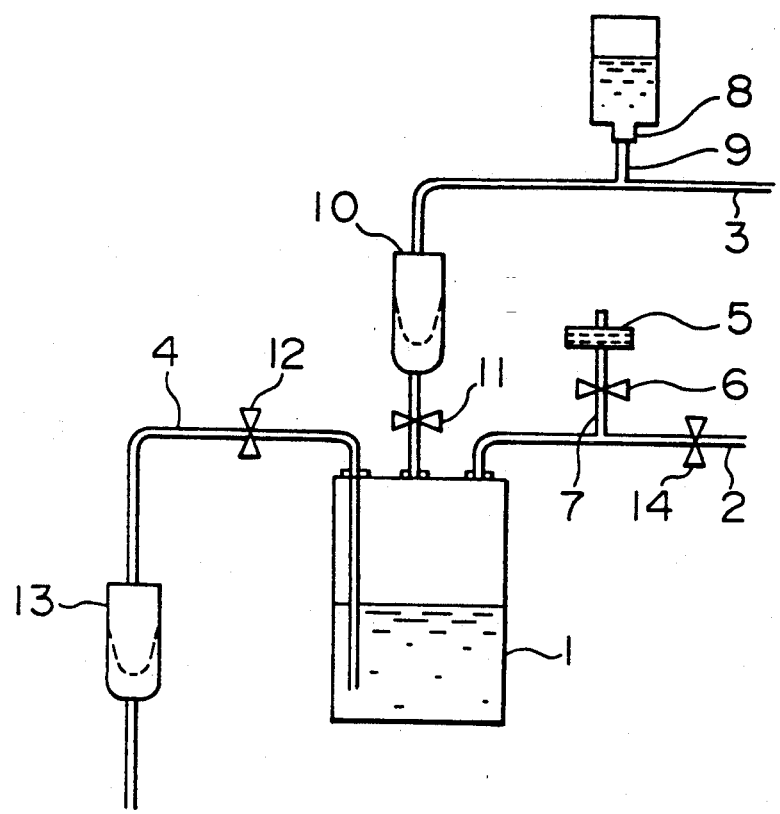
FIG. 1 is an illustration showing an overall blood collecting apparatus according to the invention.

FIG. 1 shows an arrangement of the blood collecting apparatus according to the invention. Connected to an upper part of a blood collecting container 1 are a suction pipe 2 for connection with a suction means, a collecting pipe 3 for introducing the blood, from the incised or operated part, into the collecting container 1, and a discharge pipe 4 for discharging the blood collected and reserved in the container 1.

It is possible to take any shape such as a cylinder, a sphere, a box or the like for the blood collecting container 1 but it is preferable to make it compact for easy portability. It is also desirable to make the container of a semitransparent or transparent material so as to facilitate the measurement of the collected blood and the observation of the condition thereof. There is no specific limitation to the material but the material should be light in weight and durable in deformation against a vacuum pressure. For example, it is preferable to use a hard vinyl chloride resin or the like.

Figure 5:
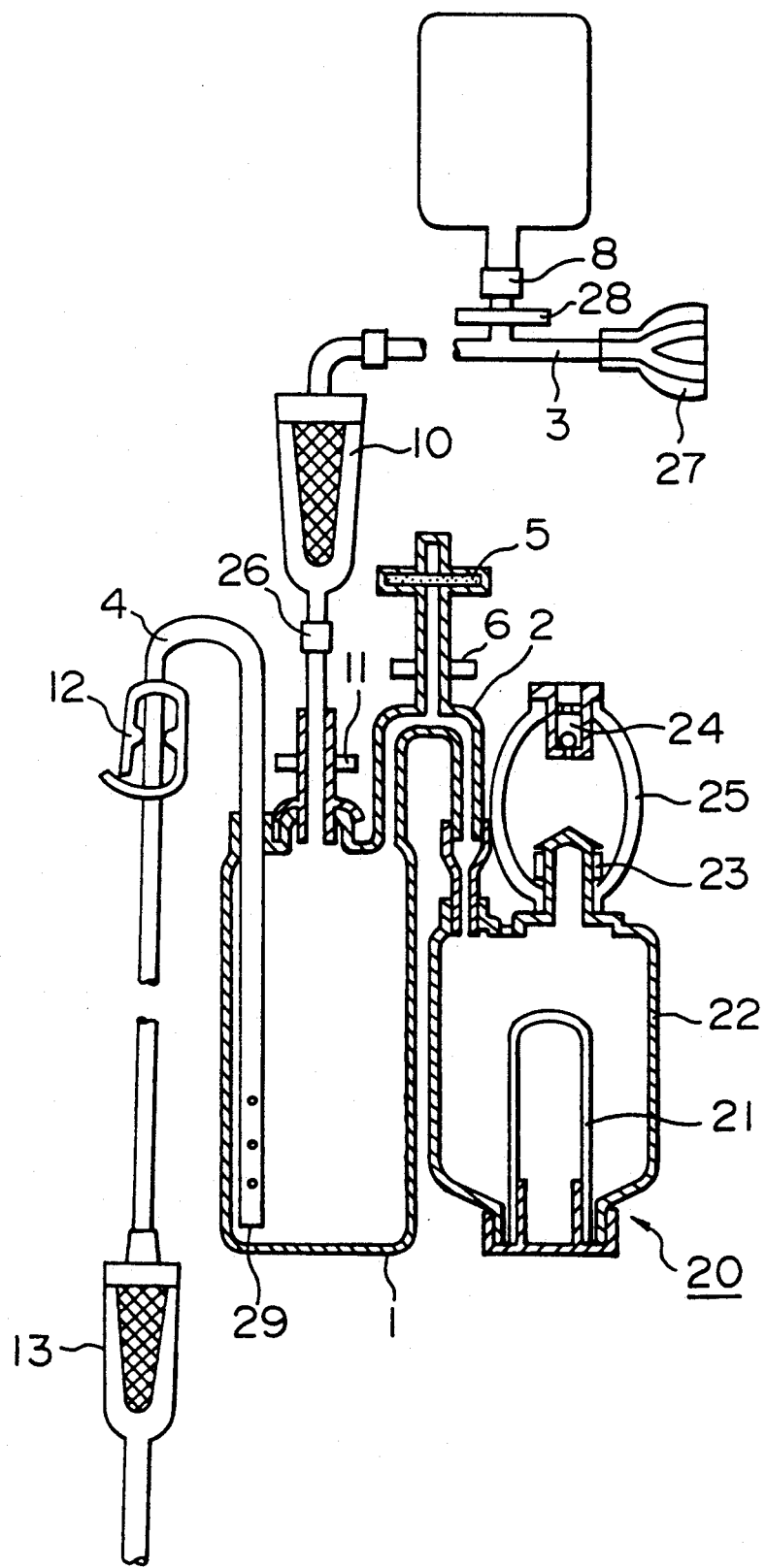
FIG. 5 is a view showing still another embodiment in which the apparatus shown in FIG. 1 is used in combination with a portable type suction means.

A catheter is connected, as desired, to the other end of the collecting pipe 3 connected to the upper part of the blood collecting container 1, for introducing the blood discharged from the incised internal part of the patient during the operation. It is sufficient to connect a single catheter to the connection part but it is also possible to connect two catheters to a connection part 27 as shown in FIG. 5. A branched pipe 9 is provided to the collecting pipe and a supply port 8 is provided for supplying an anticoagulant such as heparin added physiological saline solution. Thus, the anticoagulant is added into the blood immediately after the suction and collection, thereby prevent the generation of thrombus At the same time, valve means 6, 14, 11 and 12 provided, respectively, in the suction pipe 2, the collecting pipe 3 and the discharge pipe 4 are controlled so that it is possible to perform the processes of the collection and reserving of the blood in the blood collecting container 1 and the discharge of the blood therefrom in a completely closed system.

Figure 2:
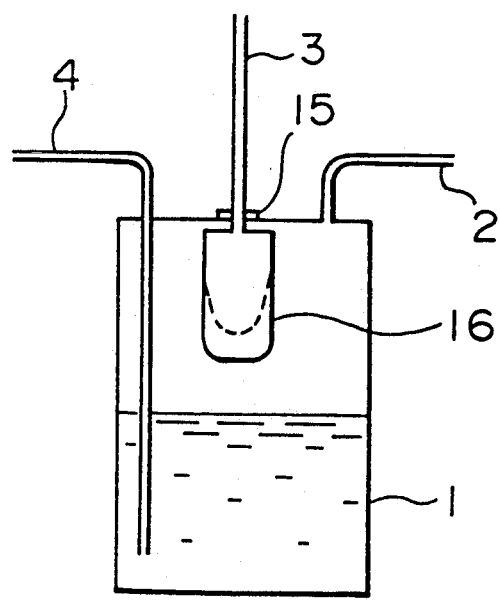
FIG. 2 is a view showing another embodiment provided with a blood filter within a blood collecting container.

A blood filter 10 and the valve means 11 are arranged in this order between the branched pipe 9 and the blood collecting container 1. The valve means 11 is used for removing blood coagulant or any other foreign objects and may be located upstream of the blood introducing inlet of the blood collecting container 1 as in the embodiment shown in FIG. 1 or within the blood collecting container as shown in FIG. 2. It is, however, preferable to use the former position to facilitate replacement due to the clogging or the like. Nevertheless, if the means is provided within the container, then, the apparatus is made compact. In either case, there are specific advantages.

It is to be noted that it is possible to change mesh roughness or filtration grade of the filters to be used, into two stages, and the two kinds of filters may be used simultaneously.

The discharge pipe 4 has one end portion connected to the upper portion of the blood collecting container 1, which end portion is further inserted into the container in the vicinity of the bottom thereof. The end portion has a suction port opened to the blood. In addition to the suction port, another suction port may be provided in a side surface in the vicinity of the end of the discharge pipe. Also, the discharge pipe 4 may be connected directly to the bottom of the blood collecting container 1. In the discharge pipe 4, there are provided valve means 12 which can be a clamp for switching over between the collection and discharge of the blood and a blood filter 13 for removing coagulant blood or the like at the other end side. These components serve to completely prevent the coagulant blood or the like from entering into the washing and condensing means, in cooperation with the blood filter 10. The outlet side of the blood filter 13 is connected to the blood washing and condensing means. It is therefore preferable to form an easy connection structure such as a lurer lock mechanism or a structure into which a needle of a transfusion filter circuit may be directly inserted.

Figure 3A:
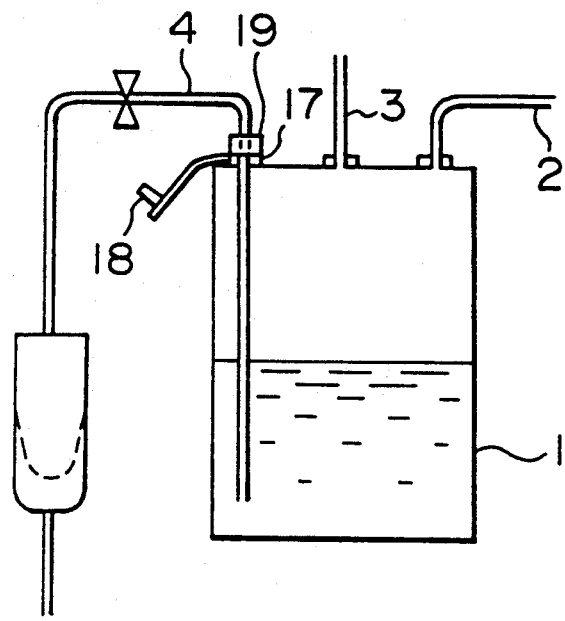
FIGS. 3A and 3B are views showing another embodiment in which a connector terminal having a cap is provided at a connection part of the upper part of the blood collecting container to the discharge pipe.
Figure 3B:
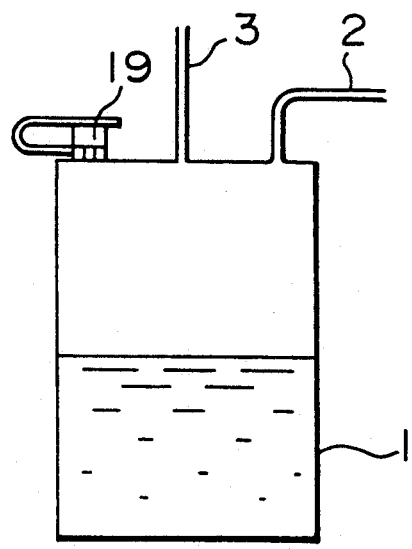

As shown in FIGS. 3A and 3B, a connector terminal 19 having a cap 18 is provided at the connection part 17 of the blood collecting container 1 to form a easy-attachment/detachment structure for the discharge pipe 4, whereby it is possible to sealingly close the connection part 17 with the cap 18 after removing the blood filter 13 during the period until a predetermined amount of blood is filled within the blood collecting container 1, or when the suction is effected for a while after the completion of the collection of the blood filter. During such a period, it is further easy to handle the blood collecting apparatus.

A relatively rough mesh filter (mesh size of 100–250 $\mu$m) is suitable for each of the blood filters 10 and 16 used in the blood collecting pipe. If the two-stage structure is used therefor as described above, it is preferable that the first stage filter is used as a prefilter having a mesh size of 0.2–0.5 m/m and the second stage filter is relatively fine to have a mesh size of 100–250 micrometers. On the other side, the blood filter has preferably a relatively fine filter (mesh size of 100 micron meters or less) In the case where the blood is returned back to the patient without using the washing and condensing apparatus, it is possible to use the filters in combination with the transfusion filters.

A valve means 14 is provided at the other end side of the suction pipe 2 and is connected to a suction means such as a suction line or a vacuum pump installed in the hospital. In this case, it is preferable to provide a pressure regulator for keeping the suction pressure at a suitable level. Also, in the case where the blood collected and reserved in the blood collecting container 1 is to be fed to the discharge pipe 4, it is necessary to perform this feeding operation under a sterile condition without directly disposing the blood to the atmosphere and to prevent bacteria, contained in the air, from being mixed into the collected blood. In any case where the blood is sucked from a pump located on the washing and condensing means or where any other method is used therefor, in order to feed the blood under the sterile condition by closing the valve means 11 of the blood collecting container 1, a sterilizing filter 5 is disposed through a valve means 6 between the blood collecting container 1 and the valve means 14 provided in the suction pipe 2. When the collected blood is to be discharged from the blood collecting container 1 to the discharge pipe 4, the valve means 6 is opened so that the sterilized air is introduced from the sterilizing filter 5, thereby the blood is smoothly sucked to be discharged.

Pinch valves or clamps may be used as the valve means 6, 11, 12, 14 used in the apparatus according to the invention.

In many usual cases, since a suction line is installed in the wall of the hospital room, the suction pipe 2 is connected to the suction line in the actual use as the suction means. However, in another case, it is possible to use a vacuum pump or a small size suction means 20 as shown in FIG. 5.

The suction means 20 shown in FIG. 5 is composed of a bottle-like hard suction container 22 incorporating an expandible balloon 21, and an elastic member such as a rubber ball 25 having an internal space provided with one-way discharge valves 23 and 24. The rubber ball 25 is firmly fixed to the upper opening port of the suction container 22 through one discharge valve 23. The elastic member having the internal space may be in the form of a spherical ball or a bellows. There is no limit therefor in configuration. This means may produce a suction pressure without any other means, and is compact to be readily portable and easy to handle.

The operation of the apparatus according to the invention will be described. First of all, the suction line arranged in the hospital room or the independent vacuum pump is used as the suction means for keeping the blood collecting container 1 at the vacuum condition.

The end of the suction, pipe 2 is connected to the suction means. The valve means 11 and 14 are opened, and at the same time, the valve means 6 and 12 are closed, so that the closed system is kept under the vacuum pressure. As a result, the blood flowing from the incised or operated part and the heparin added physiological saline solution sucked from the port 8 are collected into the blood collecting container 1 through the collecting pipe 3 and the blood filter 10. When a predetermined amount of blood containing the heparin added physiological saline solution is collected in the container, the valve means 14 is closed and the valve means 6 and 12 are opened.

Then, the blood collecting container 1 is lifted upwardly. As a result, the air is mixed into the closed system through the sterilizing filter 5, and the collected blood is discharged through the discharge pipe 4 into a bag or the like by the gravitational force. When the collected blood in the blood collecting container is discharged from the container, the container is again returned back to the original position. By operating the respective opening/closing means, the suction and collection of the blood from the incised or operated part is continued. Thus, the collection of the blood and the discharge of the blood collected in the container are alternatively performed. In this method, the valve means 11 may be dispensed with.

The valve means may be operated manually while the operator is observing the blood level within the container. If an automatic pinch valve which is controlled in associated with detecting means for detecting the blood level within the container is used as the valve means, it is possible to automatically perform the operation of collection and discharge of the blood. The blood is returned back to the patient without any separation process or the blood is separated into a blood corpuscle component and a blood plasma or serum component, whereupon the separated corpuscle component is returned back to the patient.

Figure 4:
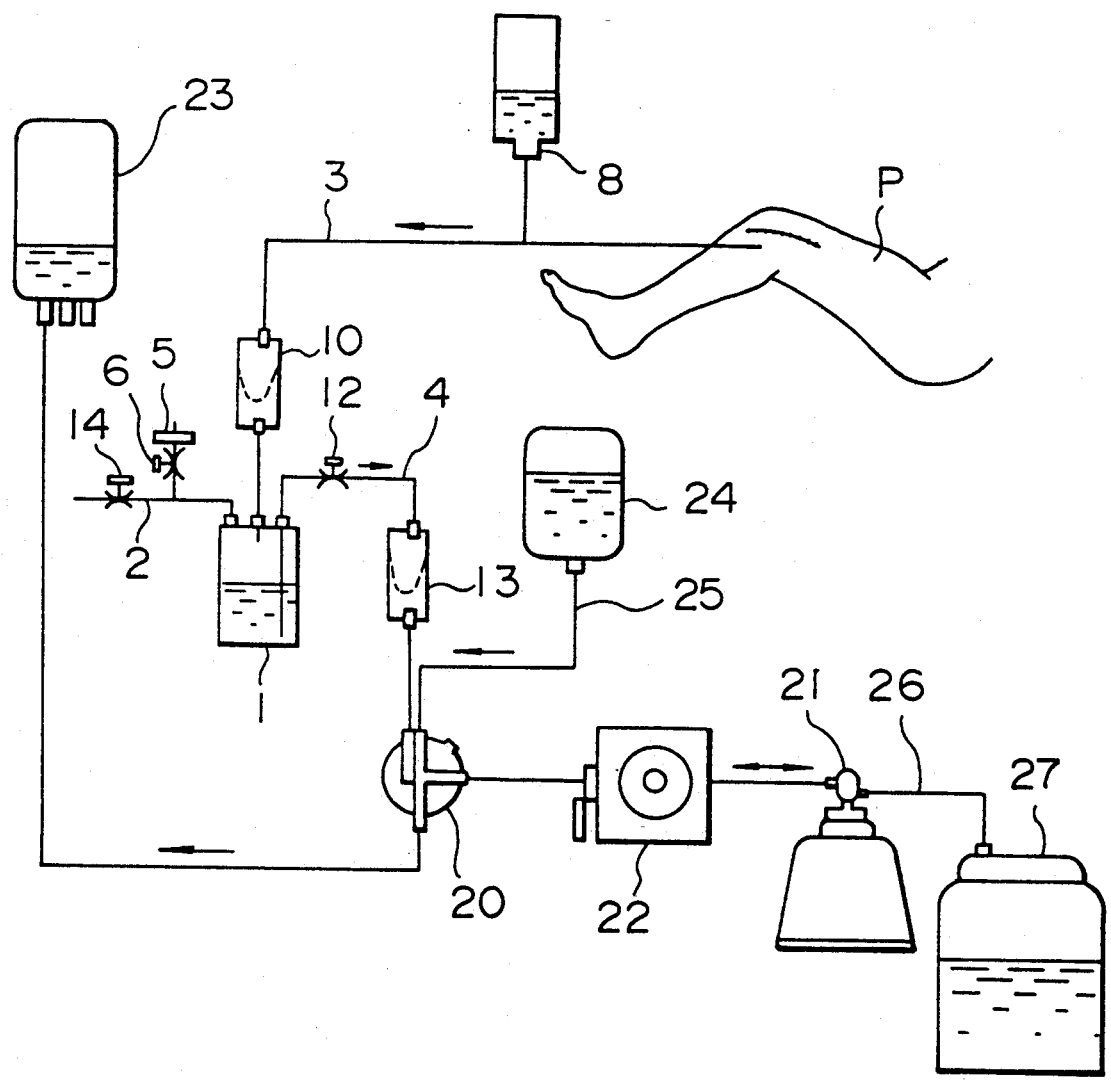
FIG. 4 is an illustration of the using method of the blood collecting apparatus, shown in FIG. 1, in combination with an apparatus for washing and condensing the collected blood.

In the case where the collected blood is washed, generally, a centrifugal separator is used. As shown in FIG. 4, the discharge pipe 4 connected to the blood collecting container 1 is connected to the centrifugal separator 21 through a switching valve 20. A roller Pump 22 which may be rotated either in a forward direction or a reverse direction is used for supplying the blood, collected in the blood collecting container 1, to the centrifugal separator 21, and for feeding the blood corpuscle components, separated by the centrifugal separator, to the bag 23. The switching valve 20 is further connected through a washing pipe 25 to a bag 24 containing therein a washing physiological saline solution.

In the apparatus shown in FIG. 4, it is possible to discharge the blood by the roller pump 22 without raising the blood collecting container 1 upwardly. The blood discharged from the container 1 by the roller pump 22 is reserved in a bowl (not shown) of the centrifugal separator 21. When a predetermined amount of blood is reserved in the bowl, the drive of the roller pump 22 is stopped, and at the same time, the centrifugal separator 21 is driven to separate the blood into the blood corpuscle component and the blood plasma component. The separated blood plasma component is discharged through a discharge pipe 26 to a bag 27. When the plasma separation has been completed and the corpuscle component has flowed to the discharge pipe 26, a sensor is operated. When the sensor is operated, the centrifugal separator is stopped. Subsequently, the switching valve 20 is operated to communicate the washing pipe 25 and the centrifugal separator 21 with each other, and the roller pump 22 is driven to feed a constant amount of washing physiological saline solution into the bowl. When the washing physiological saline solution has been fed into the bowl, the drive of the roller pump is stopped, and the centrifugal separator is again driven to wash the corpuscle component. The physiological saline solution used for washing the corpuscle component is discharged through the discharge pipe 26 to the bag 27. When the washing of the corpuscle component has been completed, and the corpuscle component has flowed to the discharge pipe, the sensor is again operated. When the sensor is operated, the switching valve 20 is switched over, thereby communicating the bag 23 and the centrifugal separator 21 with each other, and the roller pump 22 is rotated in the reverse direction, thereby feeding the corpuscle components, which has been washed, to the bag 23.

The collection of blood to the blood collecting container 1, the supply of the collected blood to the bowl of the centrifugal separator 21, the separation of the corpuscle component and the plasma component by the centrifugal separator, the washing of the separated corpuscle component with the physiological saline solution, and the discharge of the washed corpuscle component to the bag 23 are repeatedly carried out, whereby the respective steps of the collection of blood, the separation of the corpuscle component, the washing of the corpuscle component, and the reserving of the washed corpuscle component are automatically performed. The corpuscle component reserved in the bag is transfused to the patient.

In the apparatus shown in FIG. 4, the collected blood is separated into the corpuscle component and the plasma component by the centrifugal separator. It is however possible to separate the blood into the corpuscle components and the plasma component by using a plasma separator film instead of the centrifugal separator.

It is also desirable to use a suction pump, where a predetermined pressure is set up, (either type of cord supply and battery supply) as the vacuum pump for keeping the interior of the blood collecting container 1 under the vacuum pressure and sucking and collecting the discharged blood.

The operation of the apparatus when the portable type suction means 20 is used as the suction means for sucking and collecting the discharged blood will be described.

As shown in FIG. 5, the suction means 20 is connected to the suction. Pipe 2 of the blood collecting container 1, and the valves 6, 11 and 12 are closed. It should be noted that, in this case, the valve means of the suction pipe 2 may be dispensed with. Here, when a pressing/releasing operation of the rubber ball 25 is repeated, the internal air is discharged through the one-way discharge valves 23 and 24. As a result, the vacuum degree within the suction container 22 is gradually increased, so that the expandible balloon 21 incorporated in the suction means 20 is expanded. At the time when the balloon 21 is fully expanded within the suction container 22, the operation of pressing/releasing of the rubber ball 25 is stopped. Under this condition, the vacuum pressure corresponding to the shrinking force of the balloon 21 is generated within the suction container 25 and the blood collecting container 1. Subsequently, by opening the valve means 11 at the upper part of the blood collecting container 1, by the vacuum pressure within the suction means 20, the blood flowing from the incised wound of the patient is collected through the suction pipe 2 into the blood collecting container 1 together with the heparin added physiological saline solution sucked from the port 8.

The blood collecting container 1 and the suction means 20 may be detachably coupled by means of Bestro or Magic tape (registered trademark), or the blood collecting container 1 and the suction container 22 may be formed in unison in advance for easy portability, handling and operation.

According to the present invention, it is possible to collect and reserve at a suitable suction pressure the blood discharged from the patient during or after the surgical operation, to exactly control the amount of collected blood, to effectively supply a blood anticoagulant, and to effectively filtrate or remove the generated blood coagulant. Further, it is possible to carry out the switching operation in the closed system without exposing the blood to the atmosphere when the blood reserved in the container is fed to the washing and condensing means. Thus, it is possible to control or manage the sucked and reserved blood independently and safely. In addition, when the expanded balloon incorporated within the compact suction container is shrinked, if the apparatus is used in combination with the suction means which utilizes the suction force generated in the suction container, the overall apparatus is compact and portable. For instance, in a surgical operation such as plastic surgical operation, in particular, an artificial joint replacement operation or an artificial knee joint replacement operation, in which a lot of blood is discharged, the apparatus is suitable for collecting the blood flowing from the incised part after the operation because a reduced restriction is applied to the patient. Also, the apparatus according to the invention may be applied independently of the washing and condensing apparatus and is very useful in the medical field.

What is claimed is:

1. A blood collecting apparatus comprising:
    a blood collecting container for collecting blood discharged from an incised or operated part;
    a suction pipe adapted to be connected to a suction means;
    a collecting pipe for introducing the discharged blood to said blood collecting container;
    a discharge pipe for discharging the discharged blood collected in the blood collecting container;
    each of said suction pipe, said collecting pipe and said discharge pipe having one end connected to an upper part of said blood collecting container;
    said suction pipe having a first branched pipe comprising an atmospheric port, a sterilizing filter and a first valve means for opening and closing access to said first branched pipe;
    said collecting pipe having a second branched pipe provided with a port for supplying a blood anticoagulant;
    a first blood filter engaged to said collecting pipe being interposed between said second branched pipe and said blood collecting container;
    one end portion, connected to said upper portion of said blood collecting container, of said discharge pipe extending to be opened to a bottom of said container, the other end portion thereof being provided with a second blood filter;
    second valve means for opening and closing between the blood collecting container and said second blood filter;
    said sterilizing filter, said first blood filter and said second blood filter each having a mesh filter;
    a connection terminal including a cap engaged to a connection part on the upper part of said blood collecting container and to said discharge pipe; said discharge pipe extending to the bottom of said blood collecting container removable together with said second blood filter from said connection terminal, wherein said connection terminal is sealingly closeable by said cap.

2. The apparatus according to claim 1, wherein said first blood filter provided in the collecting pipe is located within said blood collecting container and below said connection part of the upper part of said blood collecting container to said collecting pipe.

3. The apparatus according to claim 1, further comprising a suction device including a suction container incorporating therein an expandable balloon, and engaged to said suction container, said elastic member having an internal space and one-way discharge valves at both ends, said elastic member being connected to an opening portion of said suction container through one of said one-way discharge valves, said suction device being air-tightly connected in fluid communication with the end of said suction pipe.

4. The apparatus according to claim 1, wherein a third valve means is provided for opening and closing access between said first branched pipe and end of the suction pipe, and a fourth valve is provided for opening and closing access between said first blood filter and said blood collecting container.

5. The apparatus according to claim 1, wherein said first blood filter is located outside and separated from said blood collecting container.

6. A method of using a blood collecting apparatus comprising the steps of:
    providing an apparatus including a blood collecting container for collecting blood discharged from an incised or operated part;
    a suction pipe adapted to be connected to a suction means;
    a collecting pipe for introducing the discharged blood to the blood collecting container;
    a discharge pipe for discharging the discharged blood collected in the blood collecting container;
    each of said suction pipe, said collecting pipe and said discharge pipe having one end connected to an upper part of said blood collecting container;
    said suction pipe having a first branched pipe comprising an atmospheric port, a sterilizing filter and a first valve means for opening and closing access to said first branched pipe;

said collecting pipe having a second branched pipe provided with a port for supplying a blood anticoagulant;

a first blood filter engaged to said collecting pipe being interposed between said second branched pipe and said blood collecting container;

one end portion, connected to said upper portion of said blood collecting container, of said discharge pipe extending to be opened to a bottom of said container, the other end portion thereof being provided with a second blood filter;

second valve means being provided for opening and closing access between the blood collecting container and said second blood filter;

said sterilizing filter said first blood filter and said second blood filter each having a mesh filter;

a connection terminal including a cap engaged to a connection part on the upper part of said blood collecting container and to said discharge pipe;

said discharge pipe extending to the bottom of said blood collecting container removable together with said second blood filter from said connection terminal;

said connection terminal sealingly closeable by said cap; and treating said blood with said apparatus.

7. The method according to claim 6, wherein said first blood filter provided in the collecting pipe is located within said blood collecting container and below said connection part of the upper part of said blood collecting container to said collecting pipe.

8. The method according to claim 5, further comprising a suction device including a section container incorporating therein an expandable balloon, and an elastic member engaged to said suction container, said elastic member having an internal space and one-way discharge valves at both ends, said elastic member being connected to an opening portion of said suction container through one of said one-way discharge valves, said suction device being air-tightly connected in fluid communication with the end of said suction pipe.

9. The method according to claim 6, wherein a third valve means is provided for opening and closing access between said first branched pipe and an end of the suction pipe, and a fourth valve means is provided for opening and closing access between said first blood filter and said blood collecting container.

10. The method according to claim 6, wherein said first blood filter is located outside and separated from said blood collecting container.

* * * * *